United States Patent
Nakamura et al.

(12) 
(10) Patent No.: US 6,476,104 B1
(45) Date of Patent: Nov. 5, 2002

(54) ANTIMICROBIAL HYDROGEL FORMING ABSORBENT POLYMERS AND PROCESS FOR MAKING THE SAME

(75) Inventors: Reiko Nakamura, Hyogo (JP); Kesyin Fugger Hsueh, Kobe (JP); Fernando Benvegnu, Maineville, OH (US); Kohtaro Fujioka, Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/601,205

(22) PCT Filed: Jan. 28, 1999

(86) PCT No.: PCT/US98/01409

§ 371 (c)(1),
(2), (4) Date: Jul. 28, 2000

(87) PCT Pub. No.: WO99/38541

PCT Pub. Date: Aug. 5, 1999

(51) Int. Cl.$^7$ ........................ C08K 5/3432; A61L 15/46
(52) U.S. Cl. .......................................... 524/99; 524/530
(58) Field of Search .................................... 524/99, 530

(56) References Cited

U.S. PATENT DOCUMENTS 6,375,939 B1 * 4/2002 Dubief ...................... 424/70.1

FOREIGN PATENT DOCUMENTS

| EP | 0 341 951 A2 | 11/1989 | ........... A61L/15/00 |
|---|---|---|---|
| EP | 0 347 199 A2 | 12/1989 | ........... A61K/7/075 |
| EP | 0 475 807 A2 | 3/1992 | ........... A61L/15/52 |

* cited by examiner

Primary Examiner—Christopher Henderson
(74) Attorney, Agent, or Firm—Joan B. Cunningham; Edward J. Milbrada; Ken K. Patel

(57) ABSTRACT

The present invention is directed to an antimicrobial hydrogel-forming absorbent polymer comprising a hydrogel-forming absorbent polymer, and an antimicrobial comprising a 1-hydroxy-2-pyrrolidone derivative represented by the formula (I);

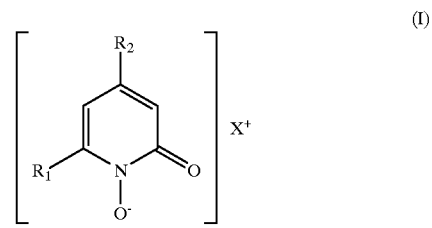

wherein $R_1$ represents an alkyl group having 1–17 carbon atoms, alkenyl group having 2–17 carbon atoms, cycloalkyl group having 5–8 carbon atoms, bicycloalkyl group having 7–9 carbon atoms, cycloalkyl-alkyl group wherein the alkyl group has 1–4 carbon atoms and the cycloalkyl group may be substituted with an alkyl group having 1–4 carbon atoms, aryl group, aralkyl group with an alkyl group having 1–4 carbon atoms, aryl-alkenyl group with the alkenyl group having 2–4 carbon atoms, aryloxyalkyl or arylmercaptoalkyl group with the alkyl group having 1–4 carbon atoms, benzhydryl group, phenylsulfonylalkyl group with the alkyl group having 1–4 carbon atoms, furylalkenyl group with the furyl or alkenyl group having 2–4 carbon atoms, wherein the above-mentioned aryl residual group may be substituted with an alkyl group having 1–4 carbon atoms, alkoxy group having 1–4 carbon atoms, nitro group, cyano group, or a halogen atom; $R_2$ represents a hydrogen atom, alkyl group having 1–4 carbon atoms, alkenyl group having 2–4 carbon atoms, halogen atom, phenyl group, or benzyl group; and $X^+$ represents an organic base, alkali metal ion, ammonium ion, alkaline earth metal ion, or a divalent to tetravalent cationic ion. The present invention further relates to a process for making such an antimicrobial hydrogel-forming absorbent polymer. The present invention further relates to a disposable absorbent article comprising an antimicrobial hydrogel-forming absorbent polymer.

13 Claims, 5 Drawing Sheets

ANTIMICROBIAL HYDROGEL FORMING ABSORBENT POLYMERS AND PROCESS FOR MAKING THE SAME

FIELD

The present invention relates to antimicrobial hydrogel-forming absorbent polymers. The invention also relates to processes for producing such absorbent polymers. The present invention has particular applicability to absorbent articles such as diapers, adult incontinence pads, sanitary napkins, and the like.

BACKGROUND

A wide variety of disposable absorbent articles designed not only to be efficient in the absorption of body fluids such as urine, blood, menses and the like, but also to be sanitary and comfortable in-use, are known in the literature. Disposable absorbent products of this type generally comprise a fluid-permeable topsheet material, an absorbent core, and a fluid-impermeable backsheet material. Various shapes, sizes and thicknesses of such articles have been explored in an attempt to make their use more comfortable and convenient.

For some time now, studies for such disposable absorbent articles have been primarily focused on the absorptive capacity of the article. As a result, various absorbent polymers with high absorptive power have been developed. Such known absorbent polymers (also known as hydrogel-forming absorbent polymers) are capable of absorbing from about thirty to sixty grams of water per gram of polymer.

More recently, research has been focused on the removal of foul odors and the prevention of skin diseases such as dermatitis, rash and redness caused by wearing a disposable absorbent article for a relatively long time. Many body fluids have an unpleasant odor, or develop such odors when in contact with air and/or bacteria for prolonged periods. Additionally, urine and/or other exudates absorbed into the absorbent article are converted to ammonia by urease produced by skin-flora, i.e., a group of normal microorganisms on the skin. This ammonia, in turn, causes dermatitis, rash and/or other forms of skin irritation. Such disease of the skin in infants can be a serious medical matter which, in extreme cases, can result in death.

Antimicrobial agents and bactericides are chemical compositions that are used to prevent microbiological contamination and deterioration of products, materials, and systems. Particular areas of application of antimicrobial agents and compositions are, for example, cosmetics, disinfectants, sanitizers, wood preservation, food, animal feed, cooling water, metalworking fluids, hospital and medical uses, plastics and resins, petroleum, pulp and paper, textiles, latex, adhesives, leather and hides, paint slurries, and disposable diapers.

For example, Japanese Patent 4-17058 discloses a disposable diaper which is said to prevent the occurrence of diaper rash caused by the growth of saprophytes such as the bacteria colibacillus and Candida. The disclosed disposable diaper consists of a water-permeable top sheet, a water-impermeable back sheet, and a water-absorbent layer sandwiched between these sheets. The water-absorbent layer is further disclosed as consisting of a) an ammonia-adsorbent, water-absorbent organic polymer selected from the group consisting of polyacrylate polymers, starch-acrylonitrile graft copolymer hydrolizates, starch-acrylic acid graft copolymers, polyvinyl alcohol-acrylate copolymers, polymers produced by further crosslinking of a crosslinked acrylate with a crosslinking agent, and modified carboxymethyl cellulose; and b) benzalkonium chloride and/or chlorhexidine gluconate, contained within the water-absorbent organic polymer. The reference further discloses forming the organic polymer/bactericide material by combining the starting materials of the organic polymer (e.g., microparticulate silicon dioxide, a copolymer such as crosslinked potassium polyacrylate, and a cross-linking agent such as ethylene glycol diglycidyl) and the bactericide. The resulting mixture is then heated to bring about a crosslinking reaction, thereby forming a crosslinked structure, the bactericide being incorporated within the structure.

While the diaper disclosed by Japanese Patent No. 4-17058 is said to result in absorption by the organic polymer of ammonia contained in the wearer's urine, and the bactericide is said to inhibit the production ammonia (formed by hydrolysis of the urea contained in the urine) by bacteria, we have discovered certain disadvantages with this technology.

For example, because such surfactant based antimicrobial agents or bactericides tend to decrease the surface tension of the liquid absorbed by the absorbent polymer or core, it was discovered that those antimicrobial agents or bactericides cause a significant re-wet or leakage problem of the liquid when they are used with a synthetic nonwoven coverstock (i.e., topsheet and/or sub-layer between topsheet and absorbent core) in disposable absorbent products. More specifically, the liquid temporarily stored in the core tends to return to the coverstock because of the lowered surface tension of the absorbed liquid by the surfactant, thereby causing the re-wet and/or leakage problems.

Based on the foregoing, there is a need for an antimicrobial hydrogel-forming absorbent polymer that minimizes the change of the surface tension of the liquid absorbed by the absorbent core.

There is also a need for an absorbent article product containing such an antimicrobial hydrogel-forming absorbent polymer, which maintains the antimicrobial activity in a region away from the wearer's skin, before and after wetting.

SUMMARY

The present invention is directed to an antimicrobial hydrogel-forming absorbent polymer comprising a hydrogel-forming absorbent polymer, and an antimicrobial comprising a 1-hydroxy-2-pyrrolidone derivative represented by the formula (I);

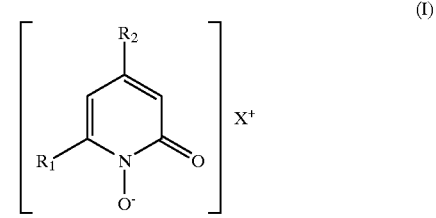

wherein $R_1$ represents an alkyl group having 1–17 carbon atoms, alkenyl group having 2–17 carbon atoms, cycloalkyl group having 5–8 carbon atoms, bicycloalkyl group having 7–9 carbon atoms, cycloalkyl-alkyl group wherein the alkyl group has 1–4 carbon atoms and the cycloalkyl group may be substituted with an alkyl group having 1–4 carbon atoms, aryl group, aralkyl group with an alkyl group having 1–4 carbon atoms, aryl-alkenyl group with the alkenyl group having 2–4 carbon atoms, aryloxyalkyl or arylmercaptoalkyl group with the alkyl group having 1–4 carbon atoms, benzhydryl group, phenylsulfonylalkyl group with the alkyl group having 1–4 carbon atoms, furylalkenyl group with the furyl or alkenyl group having 2–4 carbon atoms, wherein the above-mentioned aryl residual group may be substituted with an alkyl group having 1–4 carbon atoms, alkoxy group having 1–4 carbon atoms, nitro group, cyano group, or a halogen atom; $R_2$ represents a hydrogen atom, alkyl group having 1–4 carbon atoms, alkenyl group having 2–4 carbon atoms, halogen atom, phenyl group, or benzyl group; and $X^+$ represents an organic base, alkali metal ion, ammonium ion, alkaline earth metal ion, or a divalent to tetravalent cationic ion.

The present invention further relates to a process for making such an antimicrobial hydrogel-forming absorbent polymer, the process comprising the step of applying an antimicrobial comprising a 1-hydroxy-2-pyrrolidone derivatives represented by the formula (I) onto a hydrogel-forming absorbent polymer.

The present invention further relates to a disposable absorbent article comprising the antimicrobial hydrogel-forming absorbent polymer.

These and other features, aspects, and advantages of the present invention will become evident to those skilled in the art from a reading of the present disclosure and accompanying drawings with the appended claims.

BRIEF DESCRIPTION OF THE DRAWINGS

While the specification concludes with claims which particularly point out and distinctly claim the invention, it is believed the present invention will be better understood from the following description of preferred embodiments taken in conjunction with the accompanying drawings, in which like reference numerals identify identical elements and wherein:

DETAILED DESCRIPTION

Figure 1:
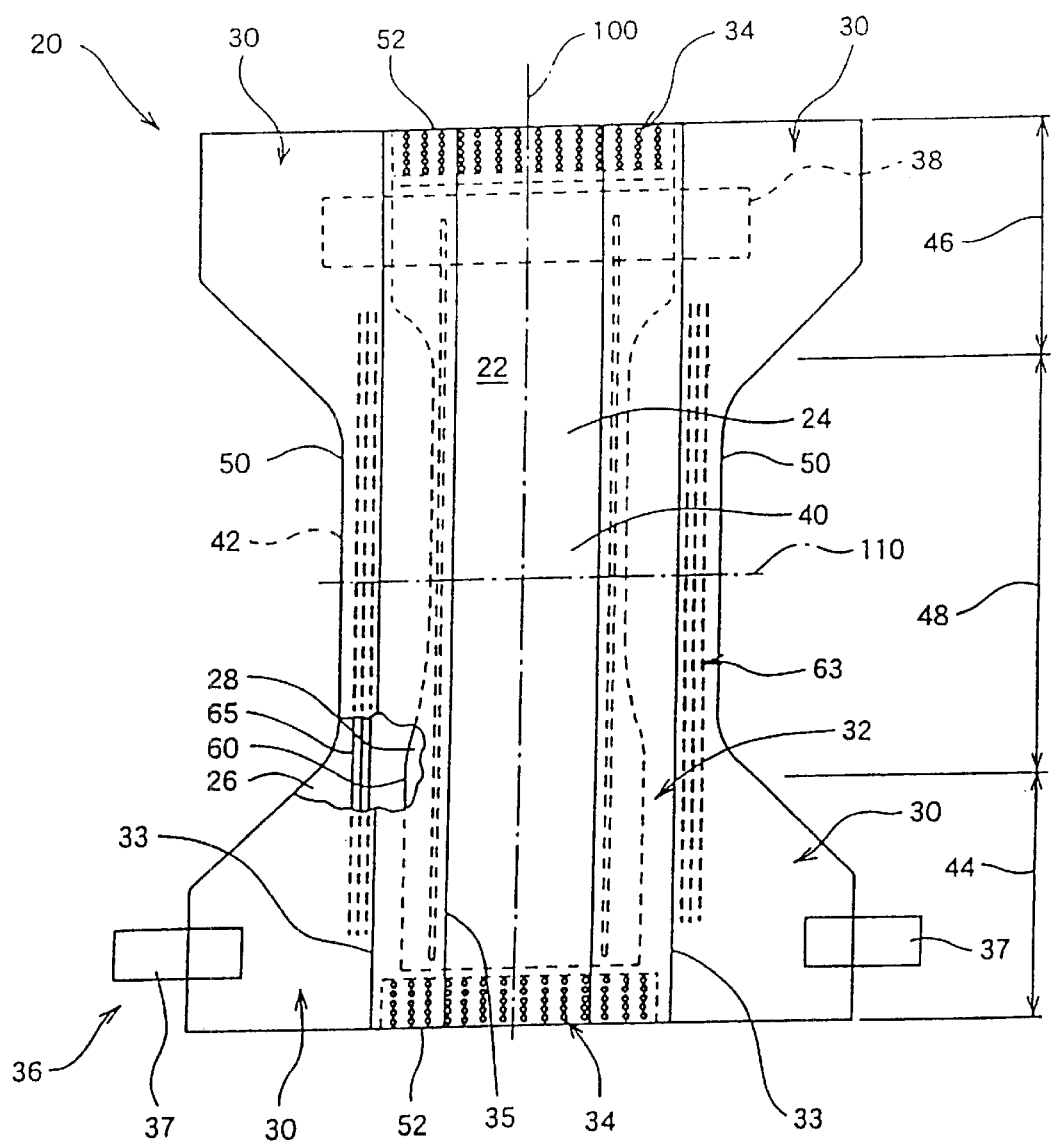
FIG. 1 is a plane view of a disposable diaper embodiment of the present invention, having portions cut away to reveal underlying structure, the inner surface of the diaper facing the viewer.

All cited references are incorporated herein by reference in their entireties. Citation of any reference is not an admission regarding any determination as to its availability as prior art to the claimed invention.

Definition

The following is a list of definitions for terms used herein.

"A-HFAP" means antimicrobial hydrogel-forming absorbent polymer. The A-HFAP contains the antimicrobial of the present invention.

"Body fluids" includes urine, menses and vaginal discharges.

"Comprising" means that other steps and other ingredients which do not affect the end result can be added. This term encompasses the terms "consisting of" and "consisting essentially of".

"Disposable" describes absorbent articles which are not intended to be laundered or otherwise restored or reused as an absorbent article (i.e., they are intended to be discarded after a single use and, preferably, to be recycled, composted or otherwise disposed of in an environmentally compatible manner).

"HFAP" means hydrogel-forming absorbent polymer. The HFAP does not contain the antimicrobial of the present invention.

"Unitary" absorbent article refers to an absorbent article which is formed of separate parts united together to form a coordinated entity so that they do not require separate manipulative parts like a separate holder and liner.

All percentages are by weight of total composition unless specifically stated otherwise.

All ratios are weight ratios unless specifically stated otherwise.

Antimicrobial Hydrogel-Forming Absorbent Polymer (A-HFAP)

The present invention relates to an antimicrobial hydrogel-forming absorbent polymer (A-HFAP) comprising a hydrogel-forming absorbent polymer (HFAP), and an antimicrobial comprising a 1-hydroxy-2-pyrrolidone derivatives represented by the formula (I) which will be described in the "2. Antimicrobial" section.

In a preferred embodiment, the A-HFAP is a mixture of the HFAP and the antimicrobial wherein the antimicrobial is generally present in the HFAP. Preferably, the weight ratio of HFAP to antimicrobial is from about 100:0.01 to about 100:2, more preferably from about 100:0.02 to about 100:1, more preferably still from about 100:0.05 to about 100:0.5.

In preferred embodiments, the HFAP is in the form of discrete units. More preferably, the HFAP particles are typically in the form of particles, sheets, films, cylinders, blocks, fibers, filaments, or other shaped elements. More preferably, the A-HFAP is particulate.

Preferably, the antimicrobial of the present invention is capable of binding to an HFAP, more preferably, capable of binding to the surface of an HFAP. In more preferred embodiments, the HFAP particles are coated with the antimicrobial. As used herein, the term "coated with" means that the antimicrobial will be on at least a portion of the surface of at least one of the particles of the HFAP. Thus, the antimicrobial may be on only some of the particles, on all of the particles, on only a portion of the surface of some or all of the particles, or onto the entire surface of some or all of the particles. Preferably, the antimicrobial is on the entire surface of most, preferably all, of the particles of the HFAP.

In preferred embodiments, the A-HFAP of the present invention has a Free-Swell Rate (FSR) of at least about 0.3 g/g/second, more preferably at least about 0.4 g/g/second. The method for measuring the FSR of the A-HFAP is described in the "Test Methods" section.

Preferably, the A-HFAP of the present invention has a Urine Surface Tension (UST) of at least about 50 dyn/cm, more preferably at least about 60 dyn/cm. The method for measuring the UST of the A-HFAP is also described in the "Test Methods" section.

In preferred embodiments, the A-HFAP of the present invention has an Antimicrobial Efficacy Index (AEI) of at least $10^2$, more preferably at least $10^3$. The method for measuring the AEI of the A-HFAP is also described in the "Test Methods" section.

1. Hydrogel-Forming Absorbent Polymer

The water-insoluble, water-swellable absorbent polymers useful in the present invention are commonly referred to as "hydrogel-forming absorbent polymers" (HFAPs), "hydrocolloids", or "superabsorbent" polymers and can include polysaccharides such as carboxymethyl starch, carboxymethyl cellulose, and hydroxypropyl cellulose; non-ionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, HFAPs useful in the present invention have a multiplicity of anionic, functional groups, such as sulfonic acid, and more typically carboxy, groups. Examples of polymers suitable for use herein include those which are prepared from polymerizable, unsaturated, acid-containing monomers. Thus, such monomers include the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing the HFAPs herein. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 (Masuda et al), issued Feb. 28, 1978; and in U.S. Pat. No. 4,062,817 (Westerman), issued Dec. 13,1977.

Olefinically unsaturated carboxylic acid and carboxylic acid anhydride monomers include the acrylic acids typified by acrylic acid itself, methacrylic acid, ethacrylic acid, 3-chloroacrylic acid, cyanoacrylic acid, methacrylic acid (crotonic acid), phenylacrylic acid, acryloloxypropionic acid, sorbic acid, chlorosorbic acid, angelic acid, cinnamic acid, p-chlorocinnamic acid, sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred HFAPs for use in the present invention contain carboxy groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. Nos. 3,661,875, 4,076,663, 4,093,776, 4,666,983, and 4,734,478.

More preferred polymer materials for use in making the HFAPs are slightly network crosslinked polymers of partially neutralized polyacrylic acids and starch derivatives thereof. More preferably, the HFAPs comprise from about 50 to about 95%, preferably about 75%, neutralized, slightly network crosslinked, polyacrylic acid (i.e., poly(sodium acrylate/acrylic acid) ). Network crosslinking renders the polymer substantially water-insoluble and, in part, determines the absorptive capacity and extractable polymer content characteristics of the HFAPs. Processes for network crosslinking these polymers and typical network crosslinking agents are described in greater detail in U.S. Pat. No. 4,076,663.

Further, surface crosslinked HFAPs can be preferably used in the present invention. They have a higher level of crosslinking in the vicinity of the surface than in the interior. As used herein, "surface" describes the outer-facing boundaries of the particle, fiber, etc. For porous HFAPs (e.g., porous particles, etc.), exposed internal boundaries can also be included. By a higher level of crosslinking at the surface, it is meant that the level of functional crosslinks for the HFAP in the vicinity of the surface is generally higher than the level of functional crosslinks for the polymer in the interior.

The gradation in crosslinking from surface to interior can vary, both in depth and profile. Thus, for example, the depth of surface crosslinking can be shallow, with a relatively sharp transition to a lower level of crosslinking. Alternatively, for example, the depth of surface crosslinking can be a significant fraction of the dimensions of the HFAP, with a broader transition.

Depending on size, shape, porosity as well as functional considerations, the degree and gradient of surface crosslinking can vary within a given HFAP. For particulate HFAPs, surface crosslinking can vary with particle size, porosity, etc. Depending on variations in surface:volume ratio within the HFAP (e.g., between small and large particles), it is not unusual for the overall level of crosslinking to vary within the material (e.g., be greater for smaller particles).

Surface crosslinking is generally accomplished after the final boundaries of the HFAP are essentially established (e.g., by grinding, extruding, foaming, etc.) However, it is also possible to effect surface crosslinking concurrent with the creation of final boundaries. Furthermore, some additional changes in boundaries can occur even after surface crosslinks are introduced.

A number of processes for introducing surface crosslinks are disclosed in the art. These include those where: (i) a di- or poly-functional reagent(s) (e.g., glycerol, 1,3-dioxolan-2-one, polyvalent metal ions, polyquaternary amines) capable of reacting with existing functional groups within the HFAP is applied to the surface of the HFAP; (ii) a di- or poly-functional reagent that is capable of reacting with other added reagents and possibly existing functional groups within the HFAP such as to increase the level of crosslinking at the surface is applied to the surface (e.g., the addition of monomer plus crosslinker and the initiation of a second polymerization reaction); (iii) no additional polyfunctional reagents are added, but additional reaction(s) is induced amongst existing components within the HFAP either during or after the primary polymerization process such as to generate a higher level of crosslinking at or near the surface (e.g., heating to induce the formation of anhydride and or esters crosslinks between existing polymer carboxylic acid and/or hydroxyl groups and suspension polymerization processes wherein the crosslinker is inherently present at higher levels near the surface); and (iv) other materials are added to the surface such as to induce a higher level of crosslinking or otherwise reduce the surface deformability of the resultant hydrogel. Combinations of these surface crosslinking processes either concurrently or in sequence can also be employed. In addition to crosslinking reagents, other components can be added to the surface to aid/control the distribution of crosslinking (e.g., the spreading and penetration of the surface crosslinking reagents.)

Suitable general methods for carrying out surface crosslinking of HFAPs according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et. al.), issued Nov. 17, 1992; published German patent application 4,020,780 (Dahmen), published Aug. 29, 1991; and published European patent application 509,708 (Gartner), published Oct. 21, 1992.

While the HFAP is preferably of one type (i.e., homogeneous), mixtures of polymers can also be used in the present invention. For example, mixtures of starch-acrylic acid graft copolymers and slightly network crosslinked polymers of partially neutralized polyacrylic acid can be used in the present invention.

The HFAP particles used in the preferred embodiments can have a size, shape and/or morphology varying over a wide range. The HFAP particles do not have a large ratio of greatest dimension to smallest dimension (e.g., granules, flakes, pulverulents, interparticle aggregates, interparticle crosslinked aggregates, and the like) and can be in the form of fibers, foams, and the like. The HFAPs can also comprise mixtures with low levels of one or more additives, such as for example powdered silica, surfactants, glue, binders, and the like. The components in this mixture can be physically and/or chemically associated in a form such that the hydrogel-forming polymer component and the non-hydrogel-forming polymer additive are not readily physically separable.

The HFAPs can be essentially non-porous or have substantial internal porosity.

For particles as described above, particle size is defined as the dimension determined by sieve size analysis. Thus, for example, a particle that is retained on a U.S.A. Standard Testing Sieve with 710 micron openings (e.g., No. 25 U.S. Series Alternate Sieve Designation) is considered to have a size greater than 710 microns; a particle that passes through a sieve with 710 micron openings and is retained on a sieve with 500 micron openings (e.g., No. 35 U.S, Series Alternate Sieve Designation) is considered to have a particle size between 500 and 710 microns; and a particle that passes through a sieve with 500 micron openings is considered to have a size less than 500 microns. The mass median particle size of a given sample of hydrogel-forming absorbent polymer particles is defined as the particle size that divides the sample in half on a mass basis, i.e., one-half of the sample by weight will have a particle size less than the mass median size and one-half of the sample will have a particle size greater than the mass median size. A standard particle-size plotting method (wherein the cumulative weight percent of the particle sample retained on or passed through a given sieve size opening is plotted versus sieve size opening on probability paper) is typically used to determine mass median particle size when the 50% mass value does not correspond to the size opening of a U.S.A. Standard Testing Sieve. These methods for determining particle sizes of the hydrogel-forming absorbent polymer particles are further described in U.S. Pat. No. 5,061,259 (Goldman et. al), issued Oct. 29, 1991.

For particles of HFAPs useful in the preferred embodiments, the particles will generally range in size from about 1 to about 2000 microns, more preferably from about 20 to about 1000 microns. The mass median particle size will generally be from about 20 to about 1500 microns, more preferably from about 50 microns to about 1000 microns, and even more preferably from about 100 to about 800 microns.

Within these size ranges, it can be preferable to choose either larger or smaller particles depending on the need for faster or slower absorption kinetics. For example, for non-porous particles, the swelling rate will generally decrease with increasing particle size. It can also be preferable to choose either larger or smaller particles or narrower size cuts (fractions) of larger or smaller particles from the bulk polymer in order to increase the gel layer permeability (i.e., increase the Saline Flow Conductivity (SFC) value). For particles of some HFAPs, it has been found that narrower size range cuts containing generally larger particle sizes within the above specified size ranges have higher SFC values without any significant degradation in other HFAP properties such as Performance Under Pressure (PUP) capacity and level of extractable polymer. Thus, for example, it can be useful to use a size cut having a mass median size in the range of from about 500 to about 710 microns wherein only minimal mass fractions of the particulates have sizes either greater than about 710 microns or less than about 500 microns. Alternatively, a broader size cut wherein the particles generally have a size in the range of from about 150 microns to about 800 microns can be useful.

2. Antimicrobial

The antimicrobial of the present invention comprises a 1-hydroxy-2-pyrrolidone derivative represented by the formula (I).

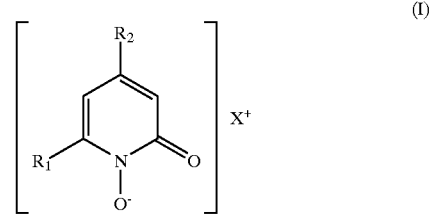

wherein $R_1$ represents an alkyl group having 1–17 carbon atoms, alkenyl group having 2–17 carbon atoms, cycloalkyl group having 5–8 carbon atoms, bicycloalkyl group having 7–9 carbon atoms, cycloalkyl-alkyl group wherein the alkyl group has 1–4 carbon atoms and the cycloalkyl group may be substituted with an alkyl group having 1–4 carbon atoms, aryl group, arylkyl group with an alkyl group having 1–4 carbon atoms, aryl-alkenyl group with the alkenyl group having 2–4 carbon atoms, aryloxyalkyl or arylmercaptoalkyl group with the alkyl group having 1–4 carbon atoms, benzhydryl group, phenylsulfonylalkyl group with the alkyl group having 1–4 carbon atoms, furylalkenyl group with the furyl or alkenyl group having 2–4 carbon atoms, wherein the above-mentioned aryl residual group may be substituted with an alkyl group having 1–4 carbon atoms, alkoxy group having 1–4 carbon atoms, nitro group, cyano group, or a halogen atom; $R_2$ represents a hydrogen atom, alkyl group having 1–4 carbon atoms, alkenyl group having 2–4 carbon atoms, halogen atom, phenyl group, or benzyl group; and $X^+$ represents an organic base, alkali metal ion, ammonium ion, alkaline earth metal ion, or a divalent to tetravalent cationic ion.

Preferred examples of the compounds represented by formula (I) includes 6-alkyl compounds such as 1-hydroxy-2-pyridone, 1-hydroxy-4-methyl-2-pyridone, 1-hydroxy-6-methyl-2-pyridone, 1-hydroxy-4,6-dimethyl-2-pyridone, 1-hydroxy-4-methyl-6-(2,4,4-trimethylpentyl)-2-pyridone; 6-cyclohexane compounds such as 1-hydroxy-4-methyl-6-cyclohex-yl-2-pyridone, 1-hydroxy-4-methyl-6-(methyl-cyclohexyl)-2-hydroxy-4-methyl-6-(2-bicyclo[2,2,1]heptyl)-2-pyridone; 6-phenyl compounds such as 1-hydroxy-4-methyl-6-(4-methyl-phenyl)-2-pyridone, 1-hydroxy-4-methyl-6-[1-(4-nitrophenoxy)-butyl]-2-pyridone, 1-hydroxy-4-methyl-6-(4-cyanophenoxymethyl)-2-pyridone, 1-hydroxy-4-methyl-6-(phenylsulfonylmethyl)-2-pyridone, 1-hydroxy-4-methyl-6-(4-bromo-benzyl)-2-pyridone, and the like. Among them, 6-alkyl compounds are preferable.

Preferably, the compounds represented by formula (I) may also be used as a salt of various organic or inorganic bases. Preferred examples of these organic bases are low molecular alkanol amines, e.g. ethanolamine, diethanolamine, N-ethylethanolamine, triethanolamine, diethylaminoethanol, 2-amino-2-methylpropanediol; non-volatile bases, e.g. ethylenediamine, hexamethylenediamine, cyclohexylamine, benzylamine, N-methylpiperazine; quaternary ammonium hydroxides, e.g. trimethylbenzyl hydroxide; guanidine and its derivatives, and especially their alkylated products; and the like. Given as examples of inorganic bases are salts of an alkali metal, e.g. sodium, potassium; ammonium salts, salts of an alkaline earth metal, e.g. magnesium, calcium; salts of a divalent to tetravalent cationic ion, e.g. zinc, aluminum, zirconium; and the like. Among the above-mentioned salts, non-volatile organic salts, e.g. low molecular alkanolamine, ethylenediamine; and inorganic salts, e.g. salts of an alkali metal are preferable.

In a preferred embodiment, the antimicrobial is piroctone olamine [1-hydroxy-4-methyl-6-(2,4,4-trimethyl pentyl)-2(1H)-pyridone monoethanolamine salt which is commercially available from Hoechst Japan Limited, Osaka, Japan under the trade name "OCTOPIROX".

The antimicrobial agent useful in the present invention may further comprise any chemical capable of preventing the growth of or killing microorganisms. Preferably, such chemical is also capable of binding to an HFAP; more preferably, capable of binding to the surface of an HFAP. Preferred antimicrobials are those that can prevent the growth of or kill microorganisms typically found in absorbent articles, more preferably those body fluids typically collected by a disposable absorbent article. Preferred antimicrobials include, but are not limited to, quaternary ammonium, phenolic, amide, acid, and nitro compounds, and mixtures thereof; more preferably quaternary ammonium, acid and phenolic; more preferably still quaternary ammonium compounds.

Preferred quaternary ammonium compounds include, but are not limited to, 2-(3-anilinovinylul)3,4-dimethyl-oxazolinium iodide, alkylisoquinolium bromide, benzalkonium chloride, benzethonium chloride, cetylpyridium chloride, chlorhexidine gluconate, chlorhexidine hydrochloride, lauryl trimethyl ammonium, methylbenzethonium chloride, stearltrimethylammonium chloride, 2,4,5-trichloro phenoxide, and mixtures thereof; more preferably benzalkonium chloride and chlorhexidine gluconate; more preferably still benzalkonium chloride.

Preferred phenolic compounds include, but are not limited to, benzyl alcohol, p-chlorophenol, chloreocresol, chloroxylenol, cresol, ocymene-5-ol (BIOSOL), hexachlorophene, hinokitiol, isopropylmethylphenol, parabens (having methyl, ethyl, propyl, butyl, isobutyl, isopropyl, and/or sodium methyl substituents), phenethyl alcohol, phenol, phenoxyethanol, o-phynylphenol, resorcin, resorcin monoacetate, sodium parabens, sodium phenolsulfonate, thioxolone, 2,4,4'-trichloro-2'-hydroxydiphenyl ether, zinc phenolsulfonate, and mixtures thereof; more preferably sodium parabens.

Preferred amides include, but are not limited to, diazolidinyl urea, 2,4-imidazolidinedione (HYDATOIN), 3,4,4'-trichlorocarbanilide, 3-trifluoromethyl-4-4'-dichlorocarbanilide, undecylenic acid monoethanolamide, and mixtures thereof; more preferably diazolidinyl urea and 2,4-imidazolidinedione; more preferably still 2,4-imidazolidinedione.

Preferred acids include, but are not limited to, benzoate, benzoic acid, citric acide, dehydroacetic acid, potassium sorbate, sodium citrate, sodium dehydroacetate, sodium salicylate, sodium salicylic acid, sorbic acid, undecylenic acid, zinc undecylenate, and mixtures thereof; more preferably benzoic acid, citric acid, salicylic acid and sorbic acid, more preferably still citric acid and sorbic acid.

Preferred nitro compounds include, but are not limited to, 2-bromo-2-nitro-2,3-propanediol (BRONOPOL), and methyldibromo glutaronitrile and propylene glycol (MERGUARD), and mixtures thereof.

Process for Producing an Antimicrobial Hydrogel-Forming Absorbent Polymer

The invention further relates to a process for making an antimicrobial hydrogel-forming absorbent polymer. The process comprises the step of applying an antimicrobial comprising a 1-hydroxy-2-pyrrolidone derivative represented by the formula (I) onto a HFAP. In preferred embodiments, the HFAP is in the form of particles as already described. Thus, in preferred embpdiments, the step of applying the antimicrobial onto the HFAP comprises the step of applying the antimicrobial onto the particles of the HFAP. As used herein, the term "applied onto" means that at least a portion of the surface area of at least one of the particles has the antimicrobial on it. Thus, the antimicrobial may be applied onto only some of the particles, onto all of the particles, onto only a portion of the surface of some or all of the particles, or onto the entire surface of some or all of the particles so that the entire surface of most, preferably all, of the particles are coated with the antimicrobial. The antimicrobial can be applied by any of various techniques and apparatus used for applying (e.g., coating) a material to another material. In another case where the antimicrobial is in the form of a liquid, the antimicrobial can be applied (e.g., coated onto the particles) by any of various techniques and apparatus used for applying a liquid to a material.

In a preferred embodiment, the antimicrobial further comprises an additional chemical that is capable of preventing the growth of or killing microorganisms as already described. In a prefferred embodiment, the step of applying the antimicrobial to the HFAP conprises the steps of mixing the additional chemical with the 1-hydroxy-2-pyrrolidone derivative represented by the formula (I), and applying the resulting mixture onto the particles. The mixing can be accomplished using various techniques and apparatus, including various mixers or kneaders, as are known in the art. It should be noted that either the 1-hydroxy-2-pyrrolidone derivative represented by the formula (I) or such mixture may be also referred as "antimicrobial" hereinafter.

In more preferred embodiments, the step of applying the antimicrobial to the HFAP conprises the steps of dissolving the antimicrobial in a solvent to make a solution, and applying the resulting solution onto the particles. The antimicrobial can be dissolved in the solvent by any of various techniques and apparatus used for dissolving a material to a solvent known in the art. In embodiments, an organic or inorganic solvents is used as the solvent. Preferably, the concentration of the antimicrobial in the solution by weight is from about 2% to 25%, more preferably, from about 5% to 15%.

In certain embodiments, an antimicrobial which is insoluble in an organic solvent can be used. In more preferred embodiments, a polar organic solvent is used as the solvent. In such embodiments, a mixture solvent of a hydrophilic organic solvent and water is used as the solvent for the antimicrobial. Non-limiting examples of the preferred organic solvent includes: the low molecular weight alcohols such as methanol, ethanol, or propanol; acetone; dimethylformamide(DMF); dimethylsulfoxide(DMSO); hexylmethylphosphoric triamide(HMPT); and mixtures thereof. In alternative preferred embodiments, non-polar solvents such as hexane, toluene, xylene, and benzene can be used as one of the organic solvents.

After preparing the solution, the solution is applied onto the particles thereby making an intermixture. More specifically, an amount of the solution is applied onto the particles of the HFAP to make an intermixture. The solution can be applied by any of various techniques and apparatus used for applying a solution to a material including coating, dumping, pouring, dropping, spraying, atomizing, condensing, or immersing the liquid mixture onto the absorbent gelling particles; to cause partial or complete coating of the HFAP with the antimicrobial. Thus, in the intermixture the solution will be on (e.g., coat) at least a portion of the surface area of the HFAP. Preferably, the solution will be on all of the surface of the HFAP particles.

The amount of the antimicrobial which is sufficient to effect an efficacious antimicrobial properties can vary based on a number of factors such as the chemical composition of the HFAP and the physical forms of the HFAP, e.g., particle size of the HFAP, and the chemical composition and molecular weight of the antimicrobial, as well as on the method of applying the antimicrobial.

In preferred embodiments, the process further comprises the step of removing at least a portion of the solvent from the intermixture. Preferably, at least about 80%, more preferably more than 95%, most preferably about 100% of the solvent is removed from the intermixture. The removal of the solvent can be made by any of various techniques and apparatus used for separating or removing liquids from liquid-solid mixtures, including evaporation, filtration, washing, or a combination thereof.

In a preferred embodiment, the antimicrobial is applied onto the HFAP after the treatment of the surface crosslinking of the HFAP particles. On the other hand, in another embodiment the antimicrobial is applied onto the HFAP before the treatment of the surface crosslinking of the HFAP. In addition, in a further embodiment the application of the antimicrobial and the treatment of the cross linking can be carried out at the same time.

In preferred embodiments, the resultant A-HFAP can have a number of shapes and sizes. For example, the A-HFAPs can be typically in the form of particles, sheets, films, cylinders, blocks, fibers, filaments, or other shaped elements. More preferably, the A-HFAP is particulate.

Absorbent Articles Employing the Antimicrobial Hydrogel-Forming Absorbent Polymer The A-HFAPs according to the present invention can be used for many purposes in many fields of use. For example, the A-HFAPs can be used for packing containers; drug delivery devices; wound cleaning devices; burn treatment devices; ion exchange column materials; construction materials; agricultural or horticultural materials such as seed sheets or water-retentive materials; and industrial uses such as sludge or oil dewatering agents, materials for the prevention of dew formation, desiccants, and humidity control materials.

Because of the unique absorbent and antimicrobial properties of the A-HFAPs of the present invention, they are especially suitable for use as absorbent cores in absorbent articles, especially disposable absorbent articles. As used herein, the term "absorbent article" refers to articles which absorb and contain body fluids and more specifically refers to articles which are placed against or in proximity to the body of the wearer to absorb and contain the various fluids discharged from the body.

In general, an absorbent article comprises: (a) a liquid permeable topsheet which is located adjacent to the wearer's body; (b) a liquid impermeable backsheet which is located distant from the wearer's body and adjacent to the wearer's clothing; and (c) an absorbent core positioned between the topsheet and the backsheet. The absorbent core comprises at least one of the above described A-HFAPs of the present invention. Preferably, the absorbent core further comprises a substrate web wherein the A-HFAP is attached to the substrate web. Alternatively, the absorbent core further comprises an envelope web encasing the A-HFAP. In a further alternative embodiment, the absorbent core further comprises two layered tissues wherein the A-HFAP is distributed between the two layered tissues.

Preferably, the A-HFAP in the absorbent core has a basis weight of from about 60 g/m$^2$ to about 1500 g/m$^2$, more preferably from about 100 g/m$^2$ to about 1000 g/m$^2$, most preferably from about 150 g/m$^2$ to about 500 g/m$^2$ of the A-HFAP.

In preferred embodiments, the absorbent core or absorbent member can further comprise fibers or fluff pulp (fibrous or fiber material), more specifically, non-absorbent-gelling fibers. Such fiber material can be used as reinforcing members in the absorbent core, improving fluid handling of the core, as well as a co-absorbent with the absorbent polymers. Preferably, the absorbent core or member includes from about 40% to about 100% by weight of the A-HFAP and from about 60% to about 0% by weight of such non-absorbent-gelling fiber material distributed within the A-HFAP.

In a preferred embodiment, the A-HFAP is in a concentration of at least 40%, more preferably from about 60 to 100% by weight in at least one region of the core or absorbent member. In a more preferred embodiment, the absorbent member comprises fibrous matrix wherein the A-HFAP is distributed in the fibrous matrix.

Any type of fiber material which is suitable for use in conventional absorbent products can be used in the absorbent core or absorbent member herein. Specific examples of such fiber material include cellulose fibers, improved cellulose fibers, rayon, polypropylene, and polyester fibers such as polyethylene terephthalate (DACRON), hydrophilic nylon (HYDROFIL), and the like. Examples of other fiber materials for use in the present invention include hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent structures, are suitable for use in the absorbent core by virtue of their good wicking properties. This is because, in the absorbent core herein, the wicking propensity of the fibers is as important, if not more important, than the absorbent capacity of the fiber material itself due to the high rate of fluid uptake and lack of gel blocking properties of the absorbent core. Synthetic fibers are generally preferred for use herein as the fiber component of the absorbent core. Most preferred are polyolefin fibers, preferably polyethylene fibers.

Other cellulosic fiber materials which can be useful in certain absorbent cores or absorbent members herein are chemically stiffened cellulosic fibers. Preferred chemically stiffened cellulosic fibers are the stiffened, twisted, curled cellulosic fibers which can be produced by internally crosslinking cellulose fibers with a crosslinking agent. Suitable stiffened, twisted, curled cellulose fibers useful as the hydrophilic fiber material herein are described in greater detail in U.S. Pat. No. 4,888,093 (Dean et al), issued Dec. 19, 1989; U.S. Pat. No. 4,889,595 (Herron et al), issued Dec. 26, 1989; U.S. Pat. No. 4,889,596 (Schoggen et al), issued Dec. 26, 1989; U.S. Pat. No. 4,889,597 (Bourbon et al), issued Dec. 26, 1989; and U.S. Pat. No. 4,898,642 (Moore et al), issued Feb. 6, 1990.

A preferred embodiment of the disposable absorbent article is a diaper. As used herein, the term "diaper" refers to a garment generally worn by infants and incontinent persons that is worn about the lower torso of the wearer. A preferred diaper configuration for a diaper comprising an absorbent core is described generally in U.S. Pat. No. 3,860,003 (Buell), issued Jan. 14, 1975. Alternatively preferred configurations for disposable diapers herein are also disclosed in U.S. Pat. No. 4,808,178 (Aziz et al), issued Feb. 28, 1989; U.S. Pat. No. 4,695,278 (Lawson), issued Sep. 22, 1987; U.S. Pat. No. 4,816,025 (Foreman), issued Mar. 28, 1989; U.S. Pat. No. 5,151,092 (Buell et al.), issued Sep. 29, 1992; and U.S. Pat. No. 5,569,234 (Buell et al.), issued Oct. 29, 1996.

A preferred embodiment of an absorbent article according to the present invention is the unitary disposable absorbent article, diaper 20, shown in FIG. 1. FIG. 1 is a plane view of the diaper 20 in its flat-out, uncontracted state (i.e., with elastic induced contraction pulled out) with portions of the structure being cut-away to more clearly show the construction of the diaper 20 and with the portion of the diaper 20 which faces the wearer, the inner surface 40, facing the viewer. As shown in FIG. 1, the diaper 20 preferably comprises a containment assembly 22 comprising a liquid permeable topsheet 24; a liquid impermeable backsheet 26 joined to the topsheet; and an absorbent core 28 positioned between the topsheet 24 and the backsheet 26. The absorbent core 28 has a pair of opposing longitudinal edges 60, an inner surface 62 and an outer surface 64. The diaper preferably further comprises side panels 30; elasticized leg cuffs 32; elasticized waistbands 34; and a fastening system 36 preferably comprising a pair of securement members 37 and a landing member 38.

The diaper 20 is shown in FIG. 1 to have an inner surface 40 (facing the viewer in FIG. 1), an outer surface 42 opposed to the inner surface 40, a rear waist region 44, a front waist region 46 opposed to the rear waist region 44, a crotch region 48 positioned between the rear waist region 44 and the front waist region 46, and a periphery which is defined by the outer perimeter or edges of the diaper 20 in which the side edges are designated 50 and the end edges are designated 52. The inner surface 40 of the diaper 20 comprises that portion of the diaper 20 which is positioned adjacent to the wearer's body during use (i.e., the inner surface 40 generally is formed by at least a portion of the topsheet 24 and other components joined to the topsheet 24). The outer surface 42 comprises that portion of the diaper 20 which is positioned away from the wearer's body (i.e., the outer surface 42 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 44 and the front waist region 46 extend from the end edges 52 of the periphery to the crotch region 48.

The diaper 20 also has two centerlines, a longitudinal centerline 100 and a transverse centerline 110. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The containment assembly 22 of the diaper 20 is shown in FIG. 1 as comprising the main body (chassis) of the diaper 20. The containment assembly 22 preferably comprises the topsheet 24, the backsheet 26 and the absorbent core 28 having a pair of opposing longitudinal edges 60, an inner surface 62, an outer surface 64. The inner surface 62 generally faces the body of the wearer while the outer surface 64 generally faces away from the body of the wearer. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 preferably comprises the topsheet 24, the backsheet 26 and the absorbent core 28 of the diaper with other features added to form the composite diaper structure.

In preferred embodiments, the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992.

The absorbent core 28 may be any absorbent member which is generally compressible, conformable, non-irritating to the wearer's skin, and capable of absorbing and retaining liquids such as urine and other certain body exudates. As shown in FIG. 1, the absorbent core 28 has a garment-facing side, a body-facing side, a pair of side edges, and a pair of waist edges. The absorbent core 28 may be manufactured in a wide variety of sizes and shapes (e.g., rectangular, hourglass, "T"-shaped, asymmetric, etc.) and, in addition to including an A-HFAP of the present invention, may also include a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20.

One embodiment of the diaper 20 has an asymmetric, modified T-shaped absorbent core 28 having ears in the front waist region but a generally rectangular shape in the rear waist region. Exemplary absorbent structures for use as the absorbent core 28 that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992.

The topsheet 24 is preferably positioned adjacent the body-facing side of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the diaper periphery and are indirectly joined together by directly joining them to the absorbent core 28 by any suitable attachment means.

The topsheet 24 is preferably compliant, soft feeling, and non-irritating to the wearer's skin. Further, the topsheet 24 is preferably liquid permeable permitting liquids (e.g., urine) to readily penetrate through its thickness. A suitable topsheet 24 may be manufactured from a wide range of materials such as woven and nonwoven materials including apertured formed materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 24 is preferably made of a hydrophobic material to isolate the wearer's skin from liquids which have passed through the topsheet 24 and are contained in the absorbent core 28 (i.e. to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991.

In a preferred embodiment, the topsheet comprises an apertured formed film. Apertured formed film materials are preferred for the topsheet because they are permeable to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991.

In an alternative preferred embodiment, the topsheet comprises an apertured formed nonwoven. Apertured formed nonwoven materials are preferred for the topsheet because they are permeable to body exudates. Suitable formed nonwoven materials are described in U.S. Pat. No. 4,840,829, entitled "Nonwoven Fabric Patterned With Apertures", which issued to Suzuki et al. on Jun. 20, 1989.

The backsheet 26 is that portion of the diaper 20 which is generally positioned away from the wearer's skin and which prevents the exudates absorbed and contained in the absorbent core 28 from wetting articles which contact the diaper 20 such as bedsheets and undergarments. Thus, the backsheet 26 is preferably impermeable to liquids (e.g., urine) and is preferably manufactured from a thin plastic film, although other flexible liquid impermeable materials may also be used. (As used herein, the term "flexible" refers to materials which are compliant and will readily conform to the general shape and contours of the human body.) However, the backsheet 26 preferably permits vapors to escape from the diaper 20. In a preferred embodiment, a microporous polyethylene film is used for the plastic film. A suitable microporous polyethylene film is manufactured by Mitsui Toatsu Chemicals, Inc., Nagoya, Japan and marketed in the trade as Espoir No. A suitable material for the backsheet 26 is a thermoplastic film having a thickness of from about 0.012 mm (0.5 mil) to about 0.051 mm (2.0 mils), preferably comprising polyethylene or polypropylene.

The backsheet 26 may comprise a single member such as the film described above, or may comprise a number of materials joined together to form the backsheet 26. For example, the backsheet may have a central region 74 comprising one film or other member and one or more outer regions 76 joined to the central region 74 comprising the same or different films or other materials. In one preferred embodiment, the backsheet 26 comprises a central region 76 comprising a liquid impermeable, non-apertured film and two opposing outer regions 76 comprising an air pervious, apertured film. The means by which any portions of such a backsheet are joined may include any means known in the art such as adhesives, heat, pressure, heat and pressure and ultrasonic bonds. Further, the backsheet 26 may comprise any number of layers of material joined together to form a laminate. If the backsheet 26 is a laminate, the layers need not be uniform throughout the backsheet. For example, the central region 74 of the backsheet 26 may comprise more layers or layers of different material than the outer regions 76.

In one preferred embodiment, the backsheet 26 comprises a plastic film (not shown) having an outer-facing surface and a body-facing surface, and a nonwoven web (not shown) joined with the outer-facing surface of the plastic film to form a laminate. Preferably, the nonwoven web covers at least a portion of the outermost portion of the diaper 20. More preferably, the nonwoven web covers at least 70% of the area of the outermost portion of the diaper 20. The nonwoven web may be joined to the plastic film by any suitable attachment means known in the art. For example, the nonwoven web may be secured to the plastic film by a uniform continuous layer of adhesive, a patterned layer of adhesive, or an array of separate lines, spirals, or spots of adhesive. Suitable adhesives include a hotmelt adhesive obtainable from Nitta Findley Co., Ltd., Osaka, Japan as H-2476-01, and a hotmelt adhesive obtainable from H. B. Fuller Japan Co., Ltd., Osaka, Japan as JM-6064. Preferably, the density of the adhesive applied between the nonwoven web and the plastic film is from about 0.05 g/m$^2$ to about 7.0 g/m$^2$, more preferably from about 0.1 g/m$^2$ to about 5.0 g/m$^2$, yet more preferably from about 0.2 g/m$^2$ to about 1.5 g/m$^2$.

Preferably, the nonwoven web may cover all or substantially all of the outer-facing surface 70 of the plastic film, or may cover only discrete predetermined portions. In a preferred embodiment, the nonwoven web covers all or substantially all of the plastic film in order to provide the diaper with a cloth-like look and feel. Further, the nonwoven web may provide the diaper with a low cost landing zone capable of engaging the hooks of a hook and loop type fastener. (Such a landing zone could be utilized as a portion of a primary fastening system or as a means for disposing of a soiled diaper.)

In a more preferred embodiment, the plastic film exists only in the containment assembly area 22 (and does not exist the side panel areas 30), while the nonwoven web exists the both of the containment assembly area 22 and the side panel areas 30. The nonwoven web covers all of the outer-facing surface 70 of the plastic film.

The nonwoven web is preferably air pervious. The nonwoven web may comprise natural fibers (e.g. cotton or wood fibers), or may comprise fibers of polyethylene, polypropylene, polyester, polyethylene terephthalate, or any combination of such fibers. Further, the nonwoven web may be carded, spunmelt, meltblown or air-through bonded or have any other characteristic or be manufactured in any manner known in the art. Preferably, the nonwoven web is comprised of sufficient thermoplastic material to allow for thermal bonding of the material to other components of the diaper.

An especially preferred nonwoven web is a spunbonded nonwoven web, preferably made of bi-component fibers. Preferably, the bi-component fiber contains a polyethylene and a polypropylene. More preferably, the bi-component fiber has a core of the polypropylene and a sheath of the polyethylene. In preferred embodiments, the bi-component fiber has from about 55% to about 95% by weight of the polyethylene. Most preferably, the bi-component fiber has from about 70% to about 90% by weight of the polyethylene.

In preferred embodiments, the spunbonded nonwoven web is placed in the disposable diaper 20 so that the fiber direction of the spunbonded bi-component plastic fibers is aligned with the longitudinal direction of the disposable diaper 20. Preferably, the spunbonded nonwoven web has a tensile strength of at least 80 gf/cm, more preferably of at least 180 gf/cm in the traverse direction of the disposable diaper 20.

An alternative preferred nonwoven web is a carded nonwoven web, preferably made of bi-component fibers. Preferably, the bi-component fiber contains a polyethylene and a polyethylene terephthalate. Preferably, the bi-component fiber has a core of the polyethylene terephthalate and a sheath of the polyethylene. In preferred embodiments, the bi-component fiber has from about 50% to about 95% by weight of the polyethylene. Most preferably, the bi-component fiber has from about 55% to about 95% by weight of the polyethylene.

In a further alternative embodiment, the bi-component fiber may contain different types of polypropylene. More preferably, the bi-component fiber has a core of the polypropylene which has a higher melting point and a sheath of the polyethylene which has a lower melting point.

In a preferred embodiment, the nonwoven web is a carded nonwoven web obtainable from Havix Co., LTD., Gifu, Japan as E-2341. The nonwoven web is made of bi-component fibers of a polyethylene (PE) and a polyethylene terephthalate (PET). The ratio of PE/PET is about 60/40. The PE/PET bi-component fiber has the dimension of 2d×51 mm.

In an alternative preferred embodiment, the nonwoven web is a spunbonded nonwoven web obtainable from Mitsui Petrochemical Industries, Ltd., Tokyo, Japan. The nonwoven web is made of bi-component fibers of a polyethylene (PE) and a polypropylene (PP). The ratio of PE/PP is about 80/20. The PE/PP bi-component fiber has the thickness is approximately 2.3d.

The backsheet 26 is preferably positioned adjacent the outer surface 64 of the absorbent core 28 and is preferably joined thereto by any suitable attachment means known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

Embodiments are also contemplated wherein the absorbent core is not joined to the backsheet 26, and/or the topsheet 24 in order to provide greater extensibility in the front waist region 46 and the rear waist region 44. Alternative embodiments are contemplated wherein an additional member, such as a liquid impermeable barrier material(s) (not shown), is positioned between the outer surface 64 of the absorbent core 28 and the backsheet 28. Any such barrier member may or may not be joined to the absorbent core 28. Further, the backsheet 26 may or may not be joined to any barrier material(s) that are positioned between the backsheet 26 and the absorbent core 28.

Another preferred embodiment of the disposable absorbent article is a catamenial product. Preferred catamenial products comprise a formed-film, apertured topsheet as disclosed in U.S. Pat. No. 4,285,343 (McNair), issued Aug. 25, 1981; U.S. Pat. No. 4,608,047 (Mattingly), issued Aug. 26, 1986; and U.S. Pat. No. 4,687,478 (Van Tilburg), issued Aug. 18, 1987.

Preferred catamenial products can comprise wings, side flaps, and other structures and elements, as described in co-pending, commonly-assigned U.S. application Ser. No. 984,071, to Yasuko Morita, entitled "Absorbent Article Having Elasticized Side Flaps", filed Nov. 30, 1992.

A particularly preferred disposable absorbent article comprising the A-HFAP of the present invention has a reduced tendency for surface wetness. Such an article also facilitates maintaining the antimicrobial as well as the absorbed liquid away from the user's skin. A disposable absorbent article comprising a backsheet, a topsheet, an acquisition/distribution layer, and an absorbent core; the absorbent core comprising the A-HFAP of the present invention.

Figure 2:
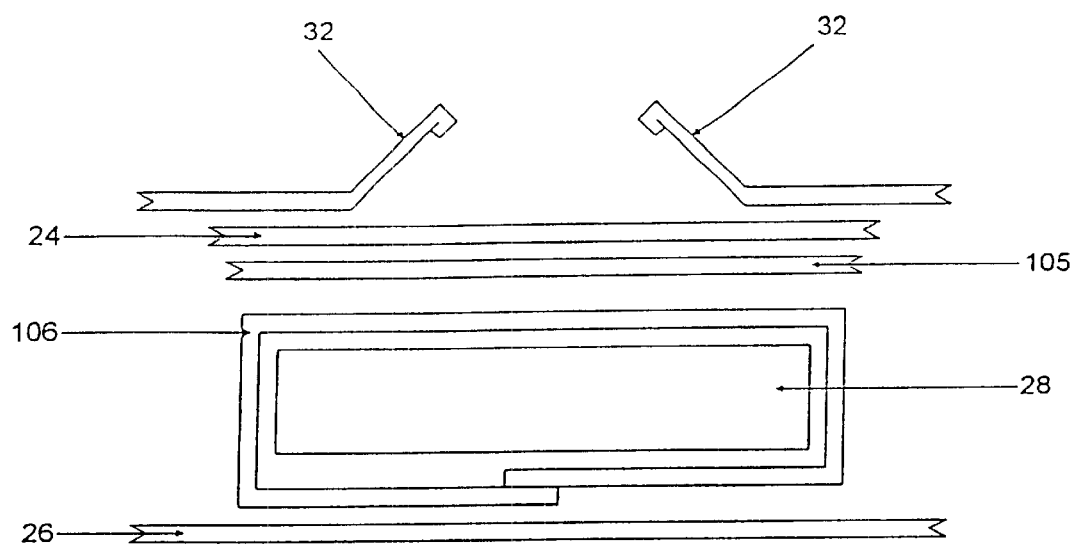
FIG. 2 is a cross-sectional view of one embodiment of the disposable diaper of FIG. 1, taken along transverse center line 110 of FIG. 1.

Referring to FIG. 2, an exemplary embodiment of such a disposable absorbent article in the form of a diaper is provided. FIG. 2 is a cross-sectional view of such an embodiment of the disposable diaper of FIG. 1, taken along transverse center line 110 of FIG. 1. This view shows fragmentary cross-sectional views of the backsheet 26, core cover 22, absorbent core 28, topsheet 24, and elasticized leg cuffs 32. This embodiment differs from that shown in FIG. 1, in that an additional element, acquisition/distribution layer 105 has been added.

Figure 3:
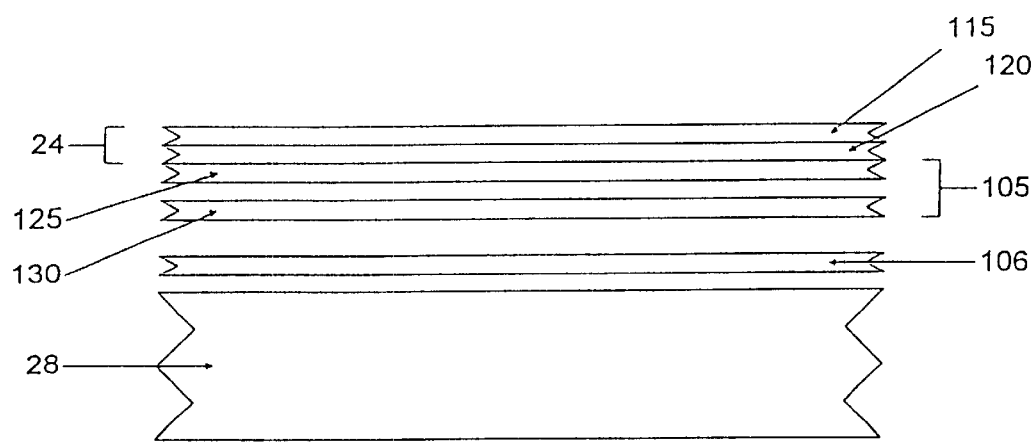
FIG. 3 is an enlarged view of an alternative embodiment of the disposable diaper of FIG. 1, the view corresponding to a portion of FIG. 2.

FIG. 3 is an enlarged view of an alternative embodiment of the disposable diaper of FIG. 1, the view corresponding to a portion of FIG. 2. In this embodiment, topsheet 24 comprises first topsheet layer 115 and second topsheet layer 120. First topsheet layer 115 and second topsheet layer 120 are preferably heat bonded together. Acquisition/distribution layer 105 comprises a first acquisition/distribution layer 125 and a second acquisition/distribution layer 130. First acquisition/distribution layer 125 is preferably spiral glue bonded to second topsheet layer 120. Preferably first acquisition/distribution layer 125 and second acquisition/distribution layer 130 are not bonded together.

Either embodiment set forth in FIG. 2 or FIG. 3 provides reduced tendency for surface wetness; and consequently facilitates maintaining the antimicrobial away from the user's skin, even after wetting. In other words, such an embodiment reduces the chance that liquid, e.g., urine having come in contact with the A-HFAP and now possibly containing antimicrobial, will flow back to the user's skin, bringing the antimicrobial in contact with the user's skin.

Preferred topsheet 24 and acquisition/distribution layer 105 materials for such a reduced surface wetness absorbent article include the following:

Preferred topsheet 24 material is P-8 nonwoven available from Fiberweb North America, Inc. (Simpsonville, S.C., U.S.A.). It is a conventional thermobonded carded web of about 20 to 22 g/m2. made of polypropylene fibers of about 2.2 dtex and an easily removable surfactant (spin finish), i.e., at a first fluid insult, it is very hydrophilic, but at repeated wetting it is essentially as hydrophobic as the base polypropylene.

More preferably, the topsheet 24 material is S-2355, available from Havix Co., Japan. This is a bi-layer composite material, and made of two kinds of synthetic surfactant treated bicomponent fibers by using carding and air-through technologies. First topsheet layer 115 is preferably a polypropylene/polypropylene bicomponent fiber, e.g., a lower melting temperature polypropylene in sheath and a higher melting temperature polypropylene in the core of the fiber. Second topsheet layer 120 is preferably a polyethylene/polyethylene telephthalate bicomponent fiber, e.g., a lower melting temperature polyethylene in the sheath and a higher melting temperature and more resilient polyethylene telephthalate in the core of the fiber. The first topsheet layer 115 preferably has a weak hydrophilic surfactant and the second topsheet layer preferably has a normal hydrophilic surfactant. The total basis weight of a typical material is about 20 to 22 $g/m^2$.

Preferably the acquisition/distribution layer 105 comprises carded, resin bonded hiloft nonwoven materials such as, for example, FT-6860, available from Polymer Group, Inc., North America (Landisiville, N.J., U.S.A.). They are made of polyethylene telephthalate fibers of 6 dtex, and has a basis weight of about 43 $g/m^2$. Alternatively, acquisition/distribution layer 105 comprises chemically treated stiffened cellulosic fiber material, available from Weyerhaeuser Co. (United States) under the trade designation of CMC. In another preferred embodiment, the acquisition/distribution layer 105 comprises conventional cellulosic fluff material, also known as wood pulp fiber, available from Weyerhaeuser Co. (United States) under the trade name FLINT RIVER.

It should be further understood that the present invention is also applicable to other absorbent articles known commercially by other names, such as incontinent briefs, adult incontinent products, training pants, diaper inserts, facial tissues, paper towels, and the like.

Test Methods (a) General

All tests are carried out at the room temperature which is about 23+/−2° C. and at about 50+/−20% relative humidity.

Unless specified explicitly, the specific synthetic urine used in the test methods is commonly known as JAYCO SYNURINE and is available from Jayco Pharmaceuticals Company of Camp Hill, Pa. The formula for the synthetic urine is: 20g/l of KCl, 2.0 g/l of $Na_2SO_4$, 0.85 g/l of $(NH_4)H_2PO_4$; 0.15 g/l $(NH_4)_2HPO_4$, 0.19 g/l of $CaCl_2$, and 0.23 g/l of $MgCl_2$. All of the chemicals are of reagent grade. The pH of the synthetic urine is in the range of from about 6.0 to about 6.4.

(b) Finished Product Wetness (Diaper Rewet)

Figure 4:
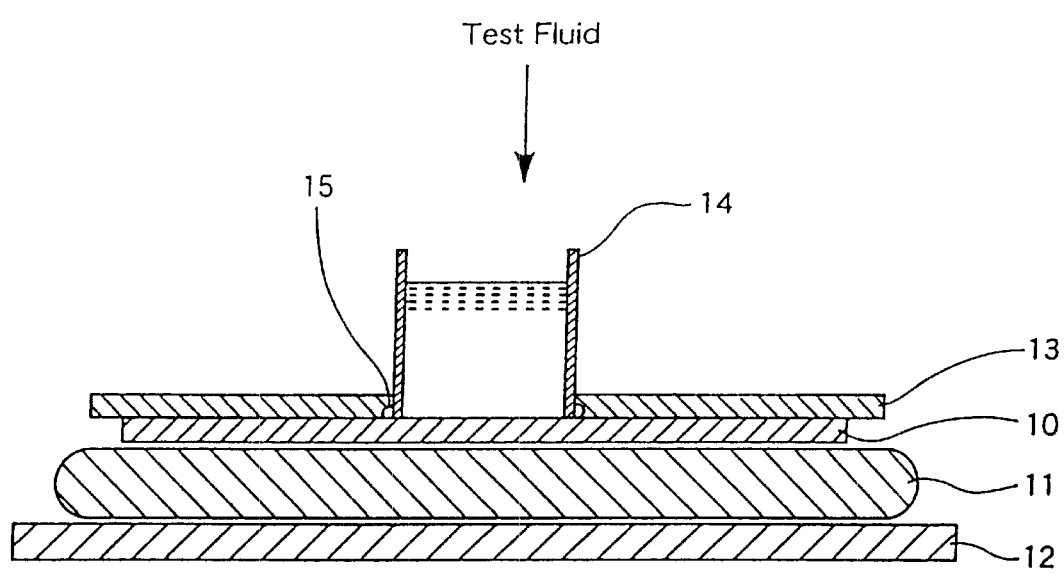
FIG. 4 shows the test device to be used in the finished product wetness test.

Referring to FIG. 4, a test sample (or an absorbent structure) 10, which comprises an absorbent core and includes a topsheet and a backsheet, is arranged to lie flat on a foam platform 11 within a perspex box (only base 12 of which is shown). A perspex plate 13 having a 5 cm diameter opening substantially in its middle is placed on top of the sample. Synthetic urine is introduced to the sample through a cylinder 14 fitted, and glued into the opening. Electrodes 15 are located on the lowest surface of the plate, in contact with the surface of the absorbent structure 10. The electrodes are connected to the timer.

The test sample 10 is loaded with 225 ml of synthetic urine from a height of 5 cm above the sample surface. The load occurs via 3 gushes, of 75 ml each, at 3 min. intervals.

Following completion of 225 ml of synthetic urine loading, the perspex plate 13 is removed. Two pieces of filter paper (supplied by Hollingsworth & Vose, United Kingdom, of the type ERT FF3.W/S), having dimensions of 12 cm by 12 cm, are weighed, and then placed on the urine loaded diaper. A load of 2 kg over a 10 cm by 10 cm area is applied to the filter paper (i.e., 0.28 psi) for 2 minutes. The filter paper is removed and weighed a second time. The Diaper Rewet (DR) is defined as the increase in weight (g) of the filter paper.

(c) Basis Weight

Basis weights are often referred to for various materials. These can be generated by essentially dividing the weight of a specimen by the area of it. The size of the area as well as the number of rewired replicates depend on the homogeneity of the specimen.

(d) Hydrophilicity/Hydrophobicity

Hydrophilicity (and hence, wettability) are typically defined in terms of contact angle and the surface tension of the fluids and solids involved. This is discussed in detail in, e.g., the American Chemical Society publication entitled "Contact Angle, Wettability and Adhesion", edited by R. F. Gould (copyright 1964). In the context of the current invention, materials can be categorized into three groups:

Materials which are "highly hydrophilic" (abbreviated "h+"): These generally have a contact angle of less than about 80 degrees. Examples include cellulosic fibers and olefinic polymers when they are treated with an effective and strong surfactant (at least when exposed the first time to wetting).

Materials which are "essentially hydrophobic" (abbreviated "h−"): These generally have a contact angle of more than about 100 degrees. Examples include pure olefines (polyethylene/polypropylene) without surfactants (neither at the surface, nor resin incorporated).

Materials which are "moderately hydrophilic" (abbreviated "ho"): These have a contact angle of about 90 degrees. Examples include polypropylene/polyethylene with less effective resin incorporated surfactants, and other less hydrophilic surfactants applied to the surface of such olefins.

(e) Surface Tension

The surface tension of the synthetic urine is measured with, for example, the Processor Tensiometer System K14 which is commercially available from KRUSS Co., Germany. The measured values of the synthetic urine and distilled water are 72 dyne/cm and 64 dyne/cm respectively.

3.0 grams of A-HFAP is put into a 400-ml beaker. 150 ml of the synthetic urine is poured into the beaker and 10 seconds is allowed for the A-HFAP to absorb some portion of the synthetic urine. The wet or swollen A-HFAP is then filtered through a filter paper (Whatman 1003-090). The filtrate is collected and immediately measured with Processor Tensiometer System K14.

(f) Free Swell Rate

The Free Swell Rate (FSR) is defined as the time length that one gram of A-HFAP absorbs 10 ml of the synthetic urine at the room temperature. The A-HFAP to be measured is in a particulate form which particle size is in the range of from about 300 to about 600 microns, and has a moisture content of less than 5 weight %.

The FSR is measured as follows. One gram of A-HFAP is spread out on the bottom of a polystylen weighing boat (5.5 cm×5.5 cm at the bottom, 2.5 cm deep, and 8.0 cm×8.0 cm at the top) which is commercially available, for example, from Iuchi Co., Ltd., Osaka, Japan as the catalogue No. 11-582-02. 10 gram of the synthetic urine is added to the weighing boat. The time required to absorb substantially all of the liquid is measured. The FSR is calculated by dividing 10 grams of the synthetic urine by 1 grams of A-HFAP and the measured time in seconds.

(g) Anti-microbial Efficacy

A fresh adult urine is first collected and filtered with a sterilized filter unit (0.45-$\mu$m pore). The inoculum is prepared by mixing three strains that are *Candida albicans* ATCC10231, *Escherichia coli* ATCC8734, and *Staphylococcus epidermis* ATCC14900. The concentration of the inoculum is adjusted to about $10^7$ cfu per 50-ml of urine. A diaper sample of 10 cm×10 cm size is placed in a sterilized, disposable petri dish. The diaper sample comprises a nonwoven topsheet, a secondary nonwoven surge layer, and an absorbent core comprising an A-HFAP (or HFAP) and a wood pulp fibers. 50 ml of the microbial spiked urine is loaded onto the diaper sample. The diaper sample is then incubated in a 33° C. oven for 10 hours and stomached in a sterilized plastic bag, which contains 150 ml of MLB/Tween broth. 10 ml of inoculum liquid is extracted from the stomached test sample. 1 ml of the inoculum extract is diluted by 10; 100; 1,000; 10,000 and 100,000 times with a MLB/Tween broth-covered petri dish. About 1 to 2 ml of the diluted in inoculum solutions is planted on a new MLB/Tween broth-covered petri dish. The inoculated petri dishes are incubated under 33° C. From these petri dishes, the bacterial population is measured by a bacterial plate counting method. The bacterial population count is performed periodically, e.g. every two or four hours.

The Anti-microbial Efficacy Index (AEI) is defined as the ratio of the bacterial population proliferated in HFAP to the bacterial population proliferated in A-HFAP over a lapse of 8 hours from the implantation.

EXAMPLES

The following examples further describe and demonstrate the preferred embodiments within the scope of the present invention. The examples are given solely for the purpose of illustration, and are not to be construed as limitations of the present invention since many variations thereof are possible without departing from its spirit and scope.

Example 1

This example shows an example of producing a HFAP of the present invention.

4,000 parts of an aqueous solution of 37 % acrylic monomer composed of 74.95 mol% of sodium acrylate, 25 mol% of acrylic acid, and 0.05 mol% of trimethylolpropane triacrylate is polymerized by being stirred with 2.0 parts of sodium persulfate and 0.08 part of 1-ascorbic acid, to produce a gel hydrated polymer finely divided in a particle diameter of about 5 mm. The gel hydrated polymer is dried with a hot air dryer at 150° C., pulverized with a hammer type pulverizing device, and sifted with a 20-mesh metallic gauze to separate a 20-mesh pass powder as an absorbent polymer A (having an average particle diameter of about 350 microns).

By mixing 100 parts of the absorbent polymer A with 0.5 part of glycerol, 2 parts of water, and 2 parts of ethyl alcohol and then heat treating the resultant mixture at 210° C., and an absorbent polymer B having the surface region thereof secondarily cross-linked is obtained. The absorbent polymer B corresponds to Code No. "L76lf" of the HFAP which is commercially available from Nippon Shokubai Co., Ltd., Osaka, Japan.

Example 2

This example shows an example of producing an A-HFAP of the present invention.

10 g of 1-hydroxy-2-pyrrolidone derivative (under trade of Octopirox, available, e.g., from Hoechst Japan (Osaka, Japan)) is dissolved into 100 ml of methyl alcohol solvent. After complete dissolution, the solution is introduced to an solution tank which is connected to a spray nozzle and air pump. 500 g of the absorbent polymer B from Example 1 is spread around on a stainless steel container. 25 g of the 1-hydroxy-2-pyrrolidone derivative solvent is sprayed onto the 500 g of absorbent polymer particles at the room temperature, and mixed by stirring for 15 minuets. The 1-hydroxy-2-pyrrolidone derivative-coated absorbent polymer particles are subsequently subjected to drying at 40° C. in a vacuumed oven for two hours, or through hot air drying for 10 minutes to reduce the moisture level to less than 1 % of the absorbent polymer particles. The particles are gently ground into granules of equal or less than 800 μm in size, resulting in nominal production of polymer dust. The resulting particles contain 0.5% 1-hydroxy-2-pyrrolidone derivative.

The resulting particles (A-HFAP) have a Free-Swell Rate (FSR) of 0.31 g/g/second, a Urine Surface Tension (UST) of 53 dyn/cm, a Diaper Rewet (DR) of 3.7 g, and an Antimicrobial Efficacy Index (AEI) of about $10^3$.

Example 3

This example shows an example of an absorbent core which contains an A-HFAP of the present invention.

A hand-sheet former is used to make a homogeneously blended pad of fibers and HAFP particles. Compressed air is used to disperse wood pulp fiber and A-HAFP particles, and a vacuum system is applied to localize the fiber and A-HAPP, and thus forming a stabilized pad. Wood pulp of Southern Pine is disintegrated and loaded connected to transfer tube by hand lifter. An A-HAFP obtained from Example 2 is first loaded on the vibration tray of the HAFP feeder and sprinkled into the wood pulp fibers (i.e., cellulose fibers) during the fiber laydown procedure. An absorbent core containing 230 to 400 g/m2 of wood pulp fibers and 160 to 360 g/m2 of the A-HFAP is formed. The absorbent core is particularly suitable for the infant and/or adult incontinent disposable diaper products. A typical composition of an L-size infant diaper application is shown in the following table 1:

TABLE 1

| Components | Weight (gm) | Percent (wt) |
| --- | --- | --- |
| Wood pulp fibers | 15 | 55 |
| Hydrogel-forming absorbent polymer (HFAP) | 12 | 44 |
| Anti-microbial | 0.024 | 0.09 |

Example 4

This example shows another example of producing an A-HFAP of the present invention.

10 g of 1-hydroxy-2-pyrrolidone derivative (under trade of Octopirox, available, e.g., from Hoechst Japan (Osaka, Japan)) is dissolved into 100 ml of methyl alcohol solvent. After complete dissolution, the solution is introduced to an solution tank which is connected to a spray nozzle and air pump. 500 g of the absorbent polymer which is commercially available from Nippon Shokubai Co., Ltd., Osaka, Japan as Code No. "L202" is spread around on a stainless steel container. 25 g of the 1-hydroxy-2-pyrrolidone derivative solvent is sprayed onto the 500 g of the absorbent polymer particles at the room temperature, and mixed by stirring for 15 minuets. The 1-hydroxy-2-pyrrolidone derivative-coated absorbent polymer particles are subsequently subjected to drying at 40° C. in a vacuumed oven for two hours, or through hot air drying for 10 minutes to reduce the methyl alcohol level to less than 1% of the absorbent polymer particles. The particles are gently ground into granules of equal or less than 800 μm in size, resulting in nominal production of polymer dust. The resulting particles contain 0.5% 1-hydroxy-2-pyrrolidone derivative.

The resulting particles (A-HFAP) have a Free-Swell Rate (FSR) of 0.45 g/g/second, a Urine Surface Tension (UST) of 61 dyn/cm, a Diaper Rewet (DR) of 0.3 g, and an Antimicrobial Efficacy Index (AEI) of about $10^3$.

Example 5

This example shows another example of an absorbent core which contains an A-HFAP of the present invention.

A hand-sheet former is used to make a homogeneously blended pad of fibers and HAFP particles. Compressed air is used to disperse wood pulp fiber and A-HAFP particles, and a vacuum system is applied to localize the fiber and A-HAPP, and thus forming a stabilized pad. Wood pulp of Southern Pine is disintegrated and loaded connected to transfer tube by hand lifter. An A-HAFP obtained from Example 4 is first loaded on the vibration tray of the HAFP feeder and sprinkled into the wood pulp fibers (i.e., cellulose fibers) during the fiber laydown procedure. An absorbent core containing 230 to 400 g/m2 of wood pulp fibers and 160 to 360 g/m2 of the A-HFAP is formed. The absorbent core is particularly suitable for the infant and/or adult incontinent disposable diaper products. A typical composition of an L-size infant diaper application is shown in the above table 1.

Example 6

This example shows an anti-microbial efficacy of an A-HFAP of the present invention, by using the in vivo test method.

An A-HFAP obtained from the Example 3 is used in the diaper sample. The bacterial population measurement is carried out according to the Anti-microbial Efficacy Test.

Figure 5:
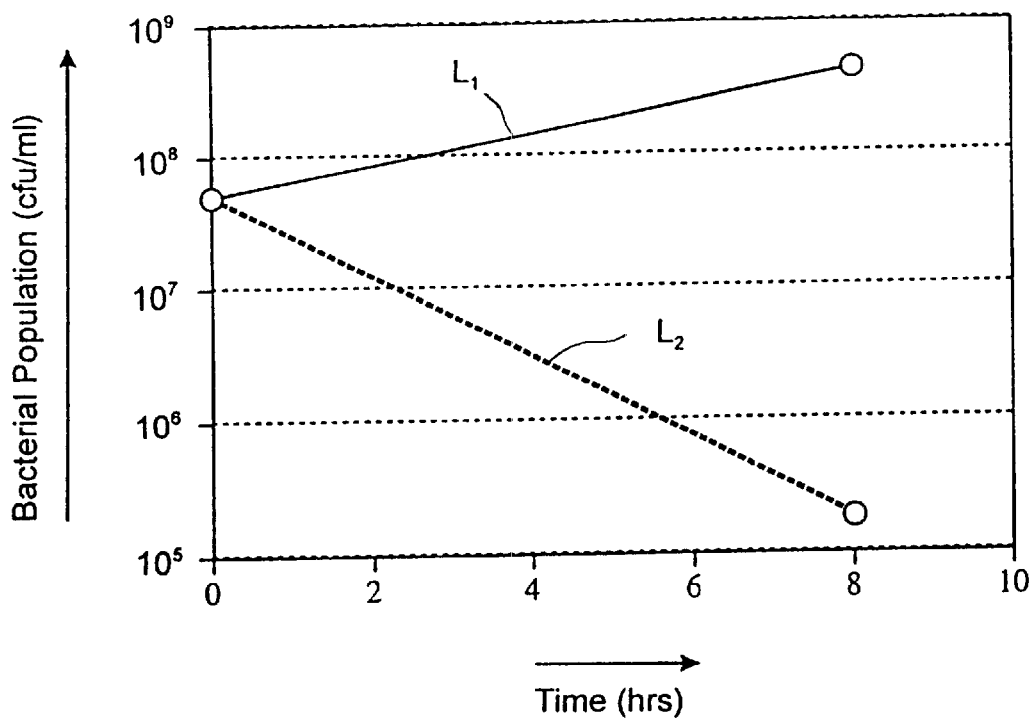
FIG. 5 is a graph showing one example of anti-microbial efficacy of the antimicrobial hydrogel-forming absorbent polymer of the invention.

FIG. 5 shows an example of an antimicrobial efficacy test result of diaper samples. The vertical axis shows the bacterial population (cfu/ml), while the horizontal axis shows the time (hours). The line L1 shows the increasing number of bacteria in the diaper sample which comprises a regular HFAP. On the other hand, the line L2 shows the increasing number of bacteria in the diaper sample which comprises an A-HFAP. As seen from FIG. 5, the number of bacteria is reduced by the efficacy of the A-HFAP.

What is claimed is:

1. An antimicrobial hydrogel-forming absorbent polymer comprising:
   a) a hydrogel-forming absorbent polymer; and
   b) an antimicrobial comprising a 1-hydroxy-2-pyrrolidone derivative represented by the formula (I);

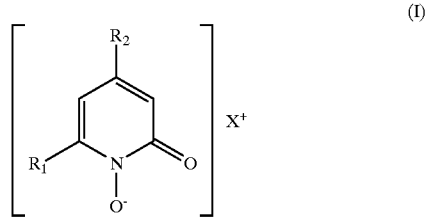

(I)

wherein $R_1$ represents an alkyl group having 1–17 carbon atoms, alkenyl group having 2–17 carbon atoms, cycloalkyl group having 5–8 carbon atoms, bicycloalkyl group having 7–9 carbon atoms, cycloalkyl-alkyl group wherein the alkyl group has 1–4 carbon atoms and the cycloalkyl group may be substituted with an alkyl group having 1–4 carbon atoms, aryl group, aralkyl group with an alkyl group having 1–4 carbon atoms, aryl-alkenyl group with the alkenyl group having 2–4 carbon atoms, aryloxyalkyl or arylmercaptoalkyl group with the alkyl group having 1–4 carbon atoms, benzhydryl group, phenylsulfonylalkyl group with the alkyl group having 1–4 carbon atoms, furylalkenyl group with the furyl or alkenyl group having 2–4 carbon atoms, wherein the above-mentioned aryl residual group may be substituted with an alkyl group having 1–4 carbon atoms, alkoxy group having 1–4 carbon atoms, nitro group, cyano group, or a halogen atom; $R_2$ represents a hydrogen atom, alkyl group having 1–4 carbon atoms, alkenyl group having 2–4 carbon atoms, halogen atom, phenyl group, or benzyl group; and $X^+$ represents an organic nitrogen base, alkali metal ion, ammonium ion, alkaline earth metal ion, or a divalent to tetravalent cationic metal ion.

2. The antimicrobial hydrogel-forming absorbent polymer of claim 1, wherein the hydrogel-forming absorbent polymer is coated with the antimicrobial.

3. The antimicrobial hydrogel-forming absorbent polymer of claim 1, wherein the antimicrobial is a piroctone olamine [1-hydroxy-4-methyl-6-(2,4,4-trimethyl pentyl)-2(1H)-pyridone monoethanolamine salt.

4. The antimicrobial hydrogel-forming absorbent polymer of claim 1, wherein the antimicrobial further comprises a chemical selected from the group consisting of quaternary ammonium, phenolic, amide, carboxylic acid, and nitro compounds, and mixtures thereof.

5. The antimicrobial hydrogel-forming absorbent polymer of claim 1, wherein the antimicrobial further comprises a benzalkonium chloride.

6. The antimicrobial hydrogel-forming absorbent polymer of claim 1, wherein the ratio of antimicrobial to the hydrogel-forming absorbent polymer is from about 100:0.01 to about 100:2.

7. A process for making an antimicrobial hydrogel-forming absorbent polymer, the process comprising the step of applying an antimicrobial comprising a 1-hydroxy-2-pyrrolidone derivative represented by the formula (I) of claim 1 onto a hydrogel-forming absorbent polymer.

8. The process of claim 7, wherein the hydrogel-forming absorbent polymer is in the form of particles, and the step of applying the antimicrobial onto the hydrogel-forming absorbent polymer comprises the step of applying the antimicrobial onto the particles.

9. The process of claim 8, wherein the step of applying the antimicrobial onto the particles comprises the step of coating the hydrogel-forming absorbent polymer with the antimicrobial.

10. The process of claim 8, wherein the step of applying the antimicrobial onto the particles comprises the steps of mixing an additional chemical that is capable of preventing the growth of or killing microorganisms with the antimicrobial, and applying the resulting mixture onto the particles.

11. The process of claim 8, wherein the step of applying the antimicrobial onto the particles comprises the steps of dissolving the antimicrobial in a solvent to make a solution, and applying the resulting solution onto the particles to make an intermixture.

12. The process of claim 11, further comprising the step of removing at least a portion of the solvent from the intermixture.

13. An antimicrobial hydrogel-forming absorbent polymer produced by the process of claim 7.

* * * * *